(12) United States Patent
Panteleon et al.

(10) Patent No.: US 12,414,709 B2
(45) Date of Patent: Sep. 16, 2025

(54) MONITORING SYSTEM AND USER INTERFACE FOR MONITORING IMPLANTABLE DISORDERED BREATHING TREATMENT SYSTEMS

(71) Applicant: ZOLL RESPICARDIA, INC., Minnetonka, MN (US)

(72) Inventors: Antonios Panteleon, Nea Penteli (GR); Kristofer J. James, Eagan, MN (US); Todd P. Goblish, Maple Grove, MN (US)

(73) Assignee: ZOLL RESPICARDIA, INC., Minnetonka, MN (US)

( * ) Notice: Subject to any disclaimer, the term of this patent is extended or adjusted under 35 U.S.C. 154(b) by 808 days.

(21) Appl. No.: 17/668,498

(22) Filed: Feb. 10, 2022

(65) Prior Publication Data

US 2022/0248978 A1 Aug. 11, 2022

Related U.S. Application Data

(60) Provisional application No. 63/148,309, filed on Feb. 11, 2021.

(51) Int. Cl.
| | |
|---|---|
| *A61B 5/08* | (2006.01) |
| *A61B 5/00* | (2006.01) |
| *A61N 1/36* | (2006.01) |
| *A61N 1/372* | (2006.01) |

(Continued)

(52) U.S. Cl.
CPC .......... *A61B 5/0826* (2013.01); *A61B 5/0022* (2013.01); *A61B 5/7435* (2013.01); *A61N 1/3611* (2013.01); *A61N 1/37247* (2013.01); *G16H 10/60* (2018.01); *G16H 20/40* (2018.01)

(58) Field of Classification Search
CPC ... A61B 5/0826; A61B 5/0022; A61B 5/4818; A61B 5/4848; A61B 5/7425; A61B 5/743; A61B 5/7435; A61N 1/3611; A61N 1/37247; G16H 10/60
See application file for complete search history.

(56) References Cited

U.S. PATENT DOCUMENTS

| | | |
|---|---|---|
| 8,233,987 B2 | 7/2012 | Gelfand et al. |
| 8,244,359 B2 | 8/2012 | Gelfand et al. |
| 8,909,341 B2 | 12/2014 | Gelfand et al. |

(Continued)

*Primary Examiner* — Carl H Layno
*Assistant Examiner* — Dhrasti Snehal Dalal
(74) *Attorney, Agent, or Firm* — Lando & Anastasi, LLP

(57) ABSTRACT

Examples of the disclosure include a method to aid user monitoring of a disordered breathing treatment, comprising providing, by an application running on a user computing device, a patient-selection screen of a graphical user interface (GUI) on a display device of the user computing device; receiving, via an input field of the patient-selection screen, an input from the user indicative of a selected patient; communicating between the user computing device and a treatment system implanted in the selected patient, responsive to receipt of the input indicative of the selected patient, to transfer patient data from the treatment system to the user computing device; and providing, by the application, a diagnostic reporting and monitoring screen including one or more graphical illustrations indicative of sleep position data for the selected patient in combination with one or more graphical illustrations of other data for the selected patient on the GUI.

20 Claims, 7 Drawing Sheets

(51) Int. Cl.
  *G16H 10/60*   (2018.01)
  *G16H 20/40*   (2018.01)

(56) References Cited

U.S. PATENT DOCUMENTS

| | | |
|---|---|---|
| 9,199,075 B1 | 12/2015 | Westlund |
| 9,468,755 B2 | 10/2016 | Westlund et al. |
| 9,744,349 B2 | 8/2017 | Westlund et al. |
| 9,987,488 B1 | 6/2018 | Gelfand et al. |
| 2008/0234556 A1 | 9/2008 | Brooke et al. |
| 2009/0099621 A1 | 4/2009 | Lin et al. |
| 2013/0267793 A1* | 10/2013 | Meador ............... A61B 5/0205 600/300 |
| 2016/0198996 A1* | 7/2016 | Dullen ............... A61B 5/6832 600/595 |
| 2016/0303388 A1* | 10/2016 | Rondoni ............ A61N 1/37247 |
| 2018/0117316 A1* | 5/2018 | Wagner ............... A61N 1/3601 |
| 2019/0365228 A1* | 12/2019 | Rondoni ............... G16H 40/67 |
| 2020/0261721 A1* | 8/2020 | Reider ............... A61B 5/1107 |
| 2020/0306538 A1 | 10/2020 | Gutierrez |
| 2020/0375549 A1* | 12/2020 | Wexler ............... A61B 5/14532 |
| 2024/0366106 A1 | 11/2024 | Panteleon et al. |

* cited by examiner

MONITORING SYSTEM AND USER INTERFACE FOR MONITORING IMPLANTABLE DISORDERED BREATHING TREATMENT SYSTEMS

CROSS-REFERENCE TO RELATED APPLICATIONS

This application claims priority under 35 U.S.C. § 119(e) to U.S. Provisional Application Ser. No. 63/148,309, titled "MONITORING SYSTEM AND USER INTERFACE FOR MONITORING IMPLANTABLE DISORDERED BREATHING TREATMENT SYSTEMS," filed on Feb. 11, 2021, which is hereby incorporated by reference in its entirety.

FIELD OF THE DISCLOSURE

The present disclosure relates to monitoring implantable disordered breathing treatment systems and devices, such as central sleep apnea (CSA) treatment systems and devices, which provide therapy to patients having a disordered breathing condition.

SUMMARY OF THE DISCLOSURE

A person's respiration is controlled by the autonomic nervous system that integrates inputs from many physiologic sensors such as mechanoreceptors and chemoreceptors. The central nervous system commands the diaphragm and other muscles in the chest as well as in the neck to physically contract and relax thus producing a breath of certain shape and tidal volume. It also acts as a respiratory pacemaker by setting the breathing rate. In a normal sleeping person, the next breath is typically initiated substantially immediately after the previous breath is completely exhaled. The term tidal volume refers to the volume of air inspired or expired during a respiratory cycle. Together tidal volume and breathing rate determine minute volume of ventilation that determines the rate at which oxygen is delivered and $CO_2$ is removed from the respiratory system.

The term disordered breathing is used herein to describe a variety of observable respiration patterns that deviate from normal respiration. For example, Cheyne-Stokes respiration ("CSR") is clinically observed and declared when a patient has bouts of "rapid" and/or "deep" breathing followed by reductions in breathing or apnea-hypopnea. This abnormal pattern of breathing can be seen in patients with strokes, traumatic brain injuries, brain tumors, and congestive heart failure and is usually a result of poor control of blood gas chemistry by the central nervous system. "Pure" Cheyne-Stokes respiration may also be called central sleep apnea (CSA) and is sometimes present with congestive heart failure. However, CSR breathing may be mixed with other respiration disorders that may or may not be related to congestive heart failure or other cardiac disorders.

Implantable systems and devices can be used to treat disordered breathing conditions such as those discussed above. For example, such systems and devices are described in U.S. Pat. No. 8,909,341 titled DEVICE AND METHOD FOR THE TREATMENT OF BREATHING DISORDERS AND CARDIAC DISORDERS; U.S. Pat. No. 8,233,987 titled RESPIRATORY RECTIFICATION; U.S. Pat. No. 8,433,412 titled MUSCLE AND NERVE STIMULATION; U.S. Pat. No. 8,244,359 titled SYSTEM AND METHOD TO MODULATE PHRENIC NERVE TO PREVENT SLEEP APNEA; U.S. Pat. No. 10,406,366 titled TRANSVENOUS PHRENIC NERVE STIMULATION SYSTEM; U.S. Pat. No. 9,744,351 titled DEVICE AND METHOD FOR THE TREATMENT OF BREATHING DISORDERS AND CARDIAC DISORDERS; and U.S. Pat. No. 9,987,488 titled DETECTING AND TREATING DISORDERED BREATHING, which are herein incorporated by reference in their entirety. Providing a clinician with information indicative a patient's responses to the treatment from such implantable systems and devices improves the care the patient receives.

Disclosed embodiments include applications, computing devices configured with the applications, and computer-implemented methods to provide user interfaces on the mobile computing devices to aid user monitoring of a disordered breathing treatment. In an exemplary embodiment, a disclosed method includes providing, by an application running on a user computing device, a patient selection screen of a graphical user interface (GUI) on a display device of the user computing device. The method also includes receiving, via an input field of the patient selection screen of the GUI, an input from the user indicative of a selected patient. Responsive to receipt of the input indicative of the selected patient, the user computing device communicates with a treatment system implanted in the selected patient to transfer patient data from the treatment system to the user computing device. The method also includes providing, by the application running on the user computing device, a diagnostic reporting and monitoring screen of the GUI on the display device. In exemplary embodiments, the diagnostic reporting and monitoring screen includes one or more graphical illustrations indicative of sleep position data for the selected patient, one or more graphical illustrations indicative of respiration synchronization data for the selected patient, one or more graphical illustrations indicative of periodic breathing data for the selected patient, one or more graphical illustrations indicative of a capture index (CI) data for the selected patient, one or more graphical illustrations of stimulation current (mA) applied to the selected patient by the treatment system, one or more graphical illustrations of respiratory sensing data for the selected patient, one or more graphical illustrations of synchronized respiratory activity data for the selected patient, and graphical representations of periodic breathing data for the patient. In some embodiments, breathing data for the patient can include data from measured signals representing patient snore sounds, patient chest movement, patient O2/desaturation, and so forth.

According to at least one aspect of the disclosure, a method to aid a user monitoring of a disordered-breathing treatment is provided, the method comprising displaying, by at least one processor on a user-computing-device screen of a user computing device, a patient-selection screen including a plurality of patient-selection fields, receiving, via the patient-selection screen, an input from the user indicative of a selection of a patient-selection field of the plurality of patient-selection fields, the selected patient-selection field corresponding to a selected patient, communicating between the user computing device and a treatment system implanted in the selected patient, responsive to receipt of the input indicative of the selection of the patient-selection field, to receive and process patient data from the treatment system to the user computing device, displaying, by the user computing device, a plurality of treatment-information fields, wherein each treatment-information field of the plurality of treatment-information fields corresponds to treatment information of the selected patient and is selectable via a respective treatment-information-field portion of the patient-selection screen, and displaying, by the user computing device responsive to detecting a user-input signal associated with a diagnostic-reporting-and-monitoring-information field of the plurality of treatment-information fields, a diagnostic-reporting-and-monitoring screen including sleep-position data indicative of a sleeping position of the selected patient, the sleep-position data being visually rendered along a time scale that includes at least a therapy time, and patient-breathing data indicative of breathing patterns of the selected patient, the patient-breathing data being visually rendered along the time scale that includes the at least the therapy time and being visually rendered relative to the sleep-position data such that the time scale of the patient-breathing data is visually aligned with the time scale of the sleep-position data.

In various examples, the patient-breathing data includes respiration-synchronization data for the selected patient. In some examples, visually rendering the patient-breathing data includes displaying the respiration-synchronization data plotted as a function of time. In at least one example, visually rendering the patient-breathing data includes displaying synchronized respiratory activity of the selected patient as a percentage. In various examples, the patient-breathing data includes periodic-breathing data for the selected patient. In some examples, visually rendering the patient-breathing data includes displaying the periodic-breathing data for the selected patient as a percentage.

In at least one example, the method includes displaying, by the user computing device and responsive to detecting a user-input signal associated with at least one of the sleep-position data or the patient-breathing data, a pop-up screen overlaying portions of the diagnostic-reporting-and-monitoring screen of the GUI on the display device, the pop-up screen visually rendering synchronized-respiratory-activity data and periodic-breathing data in relation to sleep position of the selected patient. In various examples, the patient-breathing data includes periodic-breathing data for the selected patient. In some examples, the patient-breathing data includes stimulation-energy data applied to the selected patient by the treatment system. In at least one example, the patient-breathing data includes stimulation-current data indicative of a stimulation current applied to the selected patient by the treatment system.

According to at least aspect of the disclosure, a monitoring system for monitoring disordered breathing treatment of a patient with a disordered-breathing-treatment system implanted in the patient is provided, the monitoring system comprising communication components configured to establish a communication link between the monitoring system and the disordered-breathing-treatment system implanted in the patient, a display device configured to display a graphical user interface (GUI) for use by a user of the monitoring system, and at least one processor configured to control the display device to display a patient-selection screen including a plurality of patient-selection fields, receive, via the patient-selection screen, an input from the user indicative of a selection of a patient-selection field of the plurality of patient-selection fields, the selected patient-selection field corresponding to a selected patient, communicate between the user computing device and a treatment system implanted in the selected patient, responsive to receipt of the input indicative of the selection of the patient-selection field, to receive and process patient data from the treatment system to the user computing device, control the display device to display a plurality of treatment-information fields, wherein each treatment-information field of the plurality of treatment-information fields corresponds to treatment information of the selected patient and is selectable via a respective treatment-information-field portion of the patient-selection screen, and control the display device to display, responsive to detecting a user-input signal associated with a diagnostic-reporting-and-monitoring-information field of the plurality of treatment-information fields, a diagnostic-reporting-and-monitoring screen including sleep-position data indicative of a sleeping position of the selected patient, the sleep-position data being visually rendered along a time scale that includes at least a therapy time, and patient-breathing data indicative of breathing patterns of the selected patient, the patient-breathing data being visually rendered along the time scale that includes the at least the therapy time and being visually rendered relative to the sleep-position data such that the time scale of the patient-breathing data is visually aligned with the time scale of the sleep-position data.

In various examples, the patient-breathing data includes respiration-synchronization data for the selected patient. In some examples, visually rendering the patient-breathing data includes displaying the respiration-synchronization data plotted as a function of time. In at least one example, the patient-breathing data includes periodic-breathing data for the selected patient. In various examples, the patient-breathing data includes stimulation-energy data indicative of stimulation energy applied to the selected patient by the treatment system.

According to at least one aspect of the disclosure, a non-transitory computer-readable medium storing thereon sequences of computer-executable instructions for aiding in user monitoring of a disordered-breathing treatment, the sequences of computer-executable instructions including instructions that instruct at least one processor to display, by at least one processor on a user-computing-device screen of a user computing device, a patient-selection screen including a plurality of patient-selection fields, receive, via the patient-selection screen, an input from the user indicative of a selection of a patient-selection field of the plurality of patient-selection fields, the selected patient-selection field corresponding to a selected patient, communicate between the user computing device and a treatment system implanted in the selected patient, responsive to receipt of the input indicative of the selection of the patient-selection field, to receive and process patient data from the treatment system to the user computing device, display, by the user computing device, a plurality of treatment-information fields, wherein each treatment-information field of the plurality of treatment-information fields corresponds to treatment information of the selected patient and is selectable via a respective treatment-information-field portion of the patient-selection screen, and display, by the user computing device responsive to detecting a user-input signal associated with a diagnostic-reporting-and-monitoring-information field of the plurality of treatment-information fields, a diagnostic-reporting-and-monitoring screen including sleep-position data indicative of a sleeping position of the selected patient, the sleep-position data being visually rendered along a time scale that includes at least a therapy time, and patient-breathing data indicative of breathing patterns of the selected patient, the patient-breathing data being visually rendered along the time scale that includes the at least the therapy time and being visually rendered relative to the sleep-position data such that the time scale of the patient-breathing data is visually aligned with the time scale of the sleep-position data.

In various examples, the patient-breathing data includes respiration-synchronization data for the selected patient. In some examples, visually rendering the patient-breathing data includes displaying the respiration-synchronization data plotted as a function of time. In at least one example, visually rendering the patient-breathing data includes displaying respiratory activity as a percentage. In various examples, the patient-breathing data includes periodic-breathing data for the selected patient.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "coupled" and variations thereof are used broadly and encompass both direct and indirect connections and couplings. Further, "connected" and "coupled" are not restricted to physical or mechanical connections or couplings.

Exemplary embodiments include, and operate to configure, a computer such as a tablet computer, a mobile computing device such as a smartphone, a laptop computer, a desktop computer, or other computing devices, particularly computing devices having a touch screen input GUI. The exemplary embodiments include computer-implemented methods, computer-readable media storing instructions, and configured computing devices which facilitate communication with an implanted disordered breathing treatment system and generate a graphical user interface which improves a clinician's (or other user's) ability to monitor patient response and/or acclimation to therapy provided by the implanted disordered breathing treatment system.

Although not required, disclosed embodiments are described in the general context of computer-executable instructions, such as program modules or applications, being executed by an electronic device such as a tablet computer or other computing device. Generally, program modules include routines, programs, objects, components, data structures, etc. that configure a processor or other computing device perform particular tasks. In embodiments, the disclosed embodiments may be practiced in distributed computing environments where tasks are performed by remote processing devices that are linked through a communications network. In a distributed computing environment, program modules may be located in both local and remote memory storage devices.

Figure 1:
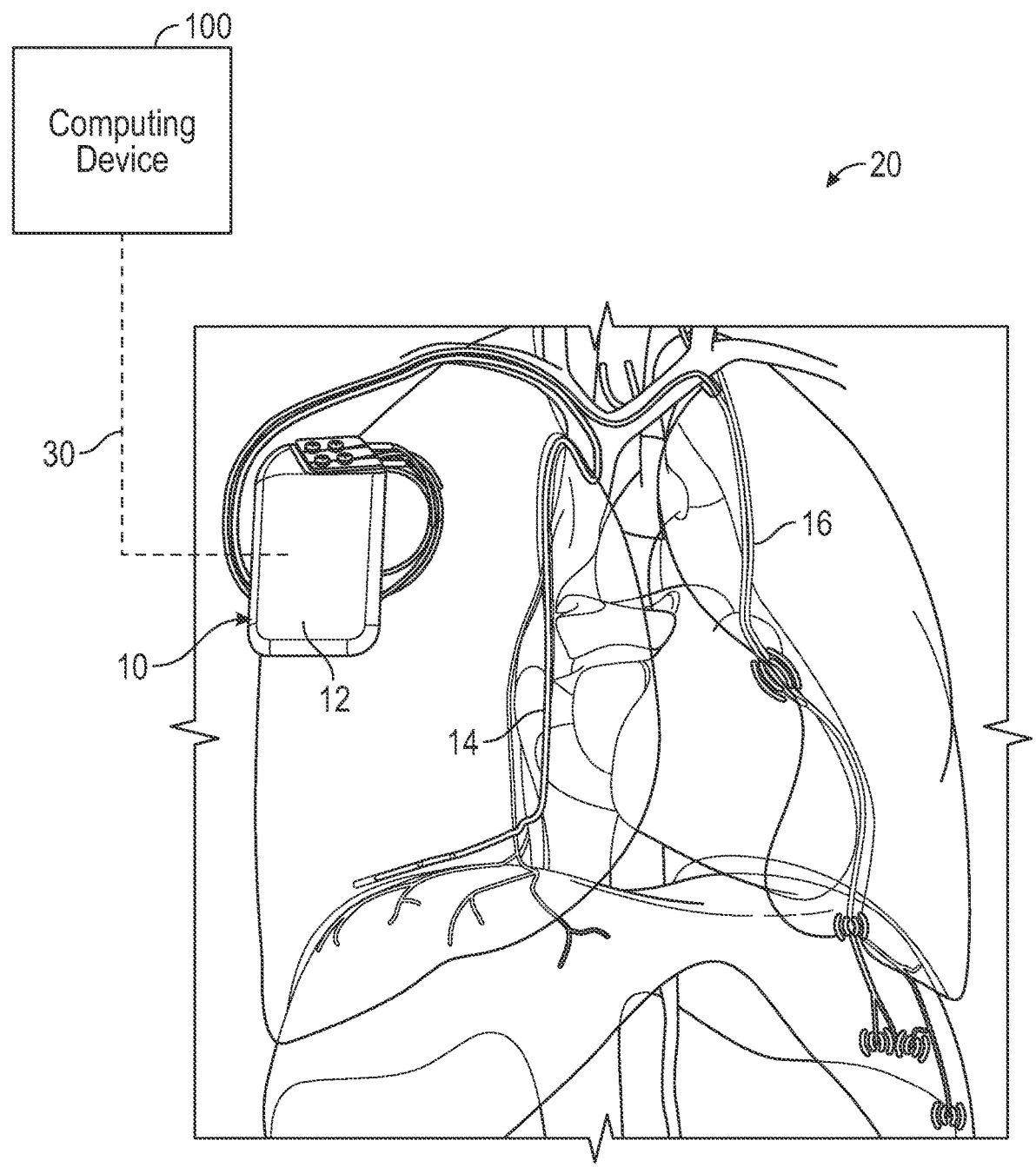
FIG. 1 is a diagrammatic illustration of a computing device, such as a tablet computer or other mobile computer, in communication with an implanted disordered breathing treatment system and configured to monitor a patient response to therapy provided by the system.

FIG. 1 illustrates a disordered-breathing treatment system 10 implanted in a patient 20. Treatment system 10 can be any suitably configured treatment system implantable in a patient for treating disordered-breathing conditions. By way of example, treatment system 10 can have features as described in any of U.S. Pat. No. 8,909,341 titled DEVICE AND METHOD FOR THE TREATMENT OF BREATHING DISORDERS AND CARDIAC DISORDERS; U.S. Pat. No. 8,233,987 titled RESPIRATORY RECTIFICATION; U.S. Pat. No. 8,433,412 titled MUSCLE AND NERVE STIMULATION; U.S. Pat. No. 8,244,359 titled SYSTEM AND METHOD TO MODULATE PHRENIC NERVE TO PREVENT SLEEP APNEA; U.S. Pat. No. 10,406,366 titled TRANSVENOUS PHRENIC NERVE STIMULATION SYSTEM; U.S. Pat. No. 9,744,351 titled DEVICE AND METHOD FOR THE TREATMENT OF BREATHING DISORDERS AND CARDIAC DISORDERS; and U.S. Pat. No. 9,987,488 titled DETECTING AND TREATING DISORDERED BREATHING. In some exemplary embodiments, treatment system 10 includes a battery-powered control device 12 which is placed under the skin in the upper chest area of the patient 20, with two thin wires or leads 14 and 16. The lead 14 may be an intravascular stimulation lead placed proximate the phrenic nerve to deliver therapy by sending signals from the control device 12 to the patient's diaphragm to stimulate breathing. The lead 16 is a transthoracic lead placed to measure transthoracic impedance to sense physiological signals such as breathing, fluid state, pulse rate, and so forth.

As shown in FIG. 1, in some exemplary embodiments, computing device 100 communicates with control device 12 of treatment system 10 through a communication connection 30. In exemplary embodiments, the communication connection 30 can be a wireless communication connection. For example, the wireless communication connection can be a Bluetooth® wireless communication connection between suitable circuitry in each of computing device 100 and the implanted control device 12 of treatment system 10. The Bluetooth connection and corresponding circuitry in each of computing device 10 and control device 12 can use Bluetooth personal area network (PAN) technology, Bluetooth Low Energy® (BLE) technology, or other Bluetooth variant technologies. BLE is a lower power variant of Bluetooth PAN technology, which uses frequency-hopping wireless technology in the 2.4 GHz unlicensed radio band to interconnect nearby devices. BLE facilitates infrequent short-range wireless data communication between devices, while utilizing very little power (for example, 0.01 to 0.5 watts). In still other embodiments, wireless connection 30 can utilize other wireless technologies and circuitry. For example, wireless connection 30 can be formed using a near-field communication (NFC) compliant technology. Near-field communication (NFC) is a set of communication protocols which enable two electronic devices to establish communication by bringing the devices within close distance of each other.

In exemplary embodiments, computing device 100 provides a display with a graphical user interface having features, as disclosed herein, that facilitate improved review of patient information by a clinician monitoring the treatment of the patient. To this end, in some exemplary embodiments, the computing device 100 is a mobile computing device such as a tablet computer, a laptop computer, and so forth, though this need not be the case in all embodiments.

Figure 2:
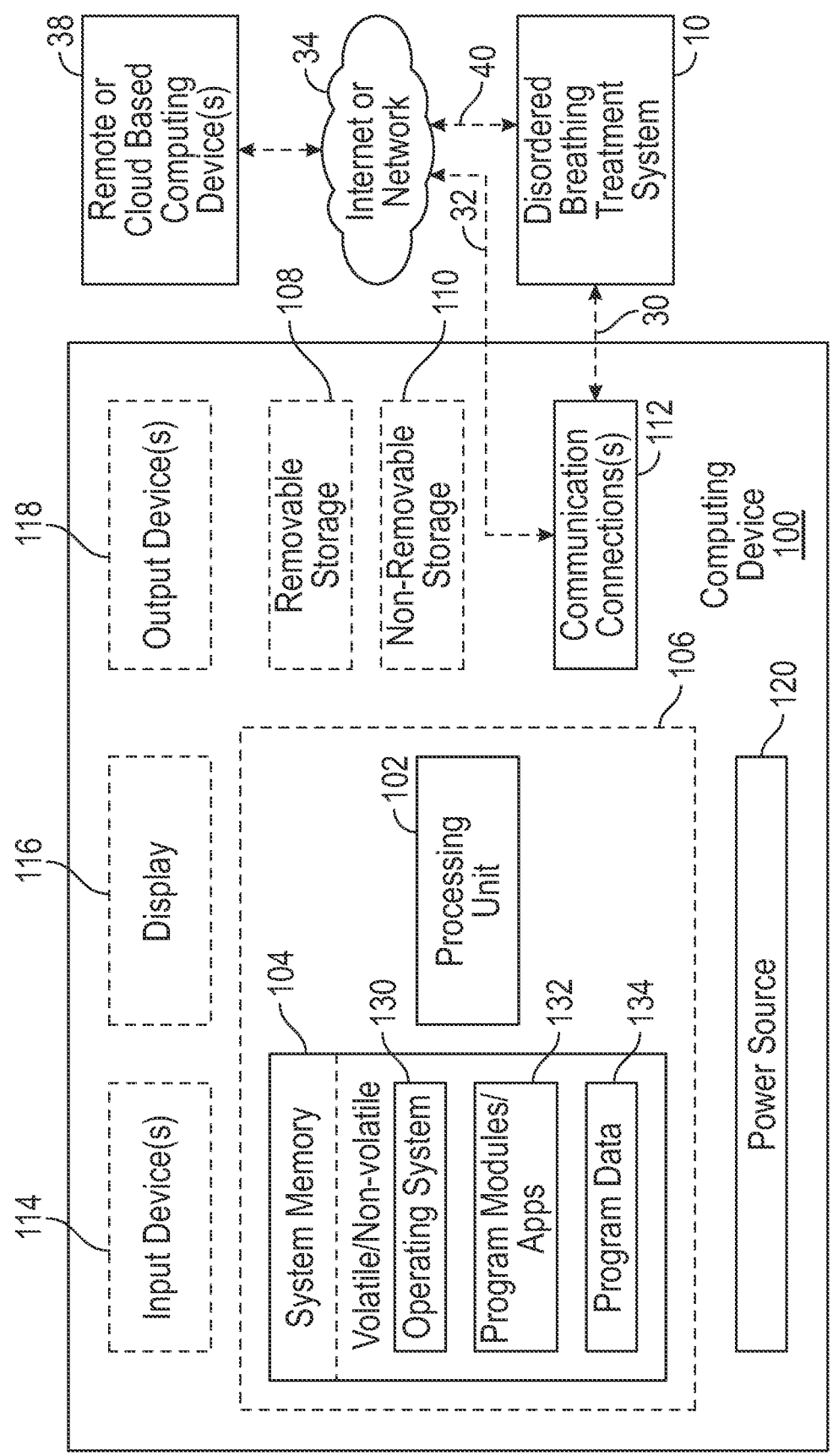
FIG. 2 is a block diagram illustrating an example embodiment of the computing device shown in FIG. 1 and configured in accordance with exemplary embodiments to monitor patient response and to generate a user interface in accordance with exemplary embodiments to provide data to a clinician or other user.

FIG. 2 shows an exemplary end-user computing device 100 for implementing certain embodiments. While in some examples the end-user device 100 is a tablet type of computer or a mobile phone such as a smart phone, device 100 can be other types of computers and is therefore described in the context of a general computing device. In its most basic configuration, the end-user device 100 includes at least a processing unit 102 and a memory 104. Depending on the exact configuration and type of computing device, the memory 104 may be volatile (such as RAM), non-volatile (such as ROM, flash memory, and so forth) or some combination of the two. This most basic configuration is illustrated in FIG. 2 by a dashed line 106.

Additionally, the device 100 may also have additional features and/or functionality. For example, the device 100 may also include additional storage (removable and/or non-removable) including, but not limited to, magnetic or optical disks or tapes, USB flash drives, memory cards, and so forth. Such additional storage is illustrated in FIG. 2 by a removable storage 108 and a non-removable storage 110. Computer-storage media may include volatile and/or nonvolatile media, removable and/or non-removable media, and so forth, implemented in any method or technology for storage of information such as computer-readable instructions, data structures, program modules or other data. The memory 104, the removable storage 108, and the non-removable storage 110 are all examples of computer-storage media. Computer-storage media includes, but is not limited to, RAM, ROM, EEPROM, flash memory or other memory technology, CDROM, digital versatile disks (DVD) or other optical storage, magnetic cassettes, magnetic tape, magnetic disk storage or other magnetic storage devices, or any other medium that can be used to store the desired information and which can be accessed by the device 100. Any such computer-storage media may be part of the device 100.

In the description that follows, disclosed embodiments will be described with reference to acts and symbolic representations of operations that are performed by one or more devices, unless indicated otherwise. As such, it will be understood that such acts and operations, which are at times referred to as being executed by a computer, include the manipulation by the processing unit of the device 100 or other disclosed devices of electrical signals representing data in a structured form. This manipulation transforms the data or maintains it at locations in the memory system of the device, which reconfigures or otherwise alters the operation of the device in a manner well understood by those skilled in the art. The data structures where data is maintained are physical locations of the memory and/or data storage that have particular properties defined by the format of the data. However, while disclosed embodiments are described in the foregoing context, it is not meant to be limiting as those of skill in the art will appreciate that various of the acts and operations described hereinafter may also be implemented in hardware or firmware.

System memory 104 may include operating system 130, one or more programming modules or applications 132, and program data 134. Operating system 130, for example, may be suitable for controlling the operation of end-user device 100. As stated above, a number of program modules 132 and data files 134 may be stored in system memory 104, including operating system 130. While executing on processing unit 102, programming modules or applications 132 may perform processes including, for example, one or more methods described herein, using one or more of the GUI screens or windows shown and described herein.

Generally, consistent with disclosed embodiments, program modules or applications may include routines, programs, components, data structures, and other types of structures that may perform particular tasks or that may implement particular abstract data types. Moreover, disclosed embodiments may be practiced with other computer system configurations, including multiprocessor systems, microprocessor-based or programmable consumer electronics, minicomputers, mainframe computers, and the like. Disclosed embodiments may also be practiced in distributed computing environments where tasks are performed by remote processing devices that are linked through a communications network. In a distributed computing environment, program modules may be located in both local and remote memory storage devices.

Furthermore, some disclosed embodiments may be practiced in an electrical circuit including discrete electronic elements, packaged or integrated electronic chips containing logic gates, a circuit utilizing a microprocessor, or on a single chip containing electronic elements or microprocessors. Some disclosed embodiments may also be practiced using other technologies capable of performing logical operations such as, for example, AND, OR, and NOT, including but not limited to mechanical, optical, fluidic, and quantum technologies. In addition, some disclosed embodiments may be practiced within a general-purpose computer or in any other circuits or systems.

Disclosed embodiments, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the disclosed embodiments may be embodied in hardware and/or in software (including firmware, resident software, micro-code, and so forth). In other words, some disclosed embodiments may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain, store, communicate, propagate, or transport the program for use by or in connection with the instruction execution system, application, apparatus, or device. Disclosed embodiments can also be implemented in a distributed computing environment using multiple computing devices in one or more on-site and/or remote locations, in a cloud-based computing environment, or in other computing environments.

The device 100 may also contain one or more communications connections 112 that allow the device to communicate with other devices. The communications connections 112 can include, for example, wired media connections such as a wired network or direct-wired connection, and wireless media connections such as acoustic, RF, infrared and other wireless media connections. In exemplary embodiments, communications connections 112 are configured to provide communication between end-user device 100 and control device 12 of treatment system 10 through the above-described communication connection 30. Thus, in exemplary embodiments, communication connections 112 includes circuitry configured to provide communication connection 30 as a wireless communication connection as described above. In still other embodiments, in which computing device 100 works with, or is replaced by, remote or cloud-based computing device(s) 38 for some or all of the processing functions described herein, communication circuitry 112 can communicate through a connection 32 and an Internet or other network 34, to the computing device(s) 38. In still other embodiments, the processing functions described herein are performed without the use of a local computing device 100, and are instead incorporated into the treatment system 10 and/or the computing device(s) 38. In such embodiments, treatment system 10 could include communication connections 40 allowing communication through the network 34 to device(s) 38. In some examples, the treatment system 10 performs at least a portion of the processing functions described herein, and a remaining portion, if any, of the processing functions may be performed by the computing device 100 and/or one or more alternative or additional computing devices, such as the remote or cloud-based computing devices 38. The following description is provided in the context of processing functions being provided at least partially by computing device 100, but those of skill in the art will understand that such functions can be implemented outside of computing device 100.

In exemplary embodiments the end-user device 100 has, or can be coupled to, a touch screen display device 116 which provides a touch-based GUI. The device 100 may also have, or be coupled to, one or more input devices 114, such as a keyboard, mouse, pen, voice input device, and so forth, for providing other input to the computing device. The device 100 may be coupled to one or more other output devices 118 such as speakers, a printer, a vibration generator, and so forth. Further, display device 116, input devices 114 and output devices 118 can all be considered to be separate from, or alternatively part of, end-user device 100.

End-user device 100 can be provided with a portable or non-portable power source 120, such as a battery pack, a transformer, a power supply, or the like. The power source 120 provides power for computations, communications and so forth by the device 100.

With control device 12 and leads 14 and 16 of treatment system 10 implanted into a particular patient 20, computing device 100 can establish communication with the control device 12 by establishing the communication connection 30, for example using a Bluetooth technology as discussed above. After establishing the communication connection 30, patient-treatment data is transferred between the control device 12 and the computing device 100. As a clinician will treat a large number of patients, in some embodiments, program modules or applications 132 of computing device 100 may configure the processing unit 102 to provide, on display device 116, a patient-selection screen, for example a patient-selection GUI screen 300, that graphically illustrates a number of patient-selection fields, for example individual patient-designation fields 305.

By selecting a particular patient-selection field from amongst a plurality of patient-selection fields displayed on a patient-selection screen, for example by touching the particular patient-selection field with a finger or a stylus or by "clicking" on the particular patient-selection field displayed on a patient-selection screen using a mouse or other pointing input device, data for a patient corresponding to the patient-selection field can be displayed. For example, a user may select a desired patient by selecting a particular patient-designation field of the patient-designation fields 305 displayed on the patient-selection GUI screen 300, such as by "clicking" the patient-designation field or touching the patient-designation field using a finger or stylus, in one example. In some embodiments, the communication connection 30 to the treatment system of a particular patient 20 is established after the patient-designation field 305 for that particular patient is selected by the clinician or user. For example, the communication connection 30 to the treatment system of the particular patient 20 may be established responsive to receiving an input (for example, a "clicking" input, a touch input, and so forth) indicative of a selection of a patient-selection field, such as a selection of a patient-designation field of the patient-designation fields 305. In other embodiments, the computing device 100 can have established, previously or in an on-going fashion, communication connections to multiple treatment systems each implanted in a different patient.

Upon patient selection, program modules or applications 132 of computing device 100 may configure the processing unit 102 to provide, on display device 116, a plurality of selectable treatment-information fields, each corresponding to respective treatment information for the selected patient. In one example, the treatment-information fields may each be represented by selectable information tabs on a GUI, and each treatment-information field may correspond to, and be selectable via, a respective treatment-information-field portion of the GUI. For example, the processing unit 102 may be configured to provide, on display device 116, a default GUI screen with multiple different treatment-information fields, or tabs, from which the clinician or user can select corresponding different GUI screens relating to the patient, the patient's implanted-treatment system, or other information. Each of the treatment-information fields may be displayed at, and selectable via a respective treatment-information-field portion of, the GUI screen.

Figure 4:
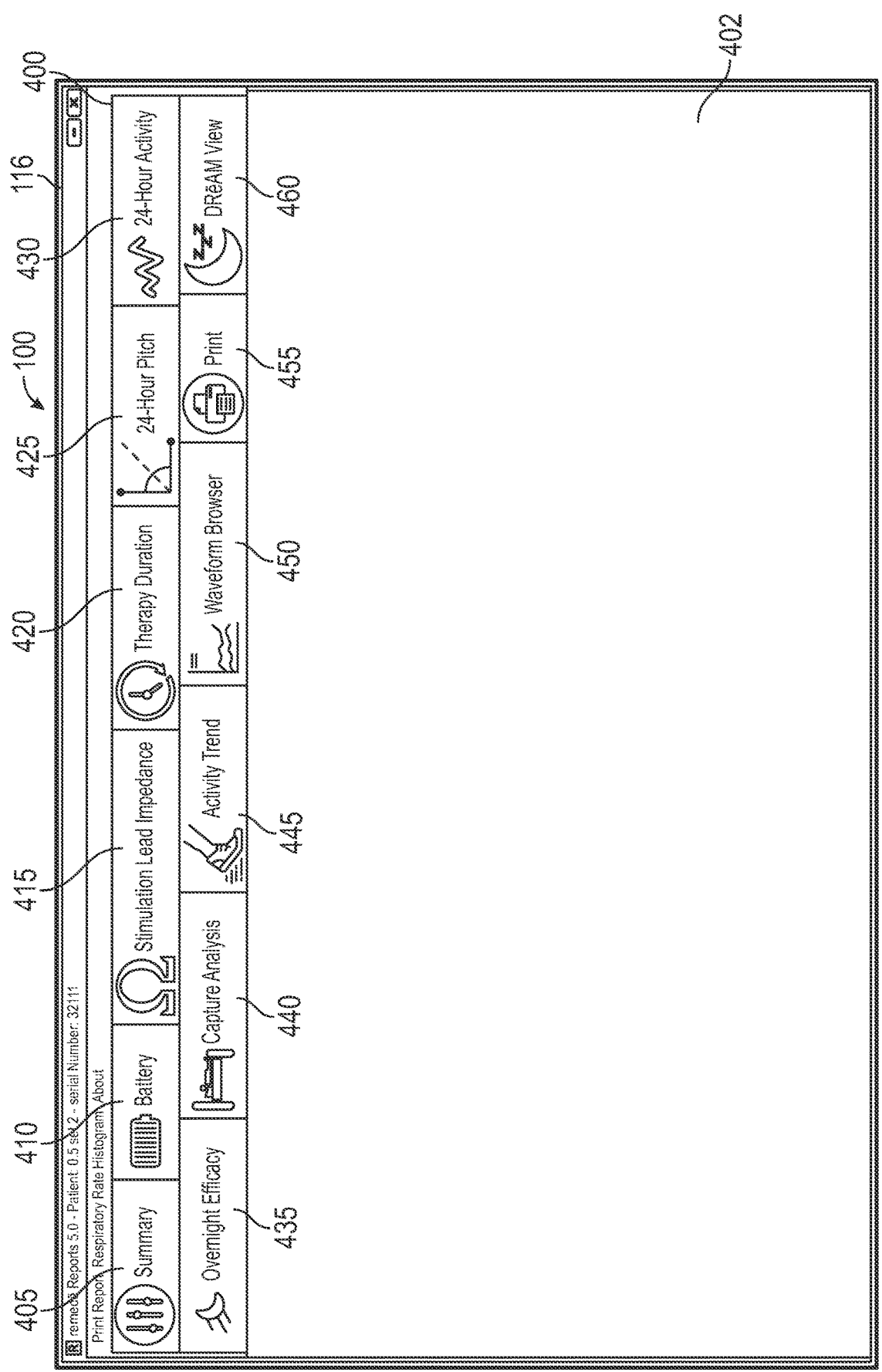
FIG. 4 is an illustration of a portion of an exemplary default GUI screen, which the computing device shown in FIGS. 1 and 2 is configured to display, for a particular selected patient.

A portion of an example GUI screen 400 is shown in FIG. 4. The GUI screen 400 may provide a plurality of treatment-information fields, for example tabs 405-460, each corresponding to the patient's therapy information and being displayed at, and selectable via, a respective treatment-information-field portion of the GUI screen 400. In an example embodiment, the GUI screen 400 for a particular selected patient displays a summary GUI screen by default. The summary GUI screen may correspond to a summary treatment-information field, for example a "Summary" tab 405, and may include in screen area 402 various summary information for the patient's treatment. The summary information is omitted in FIG. 4 to simplify the illustration of the GUI. In other examples, other treatment information corresponding to other treatment-information fields may be displayed on the GUI screen 400 by default.

In an example embodiment, other selectable treatment-information fields illustrated on the GUI screen 400, as well as on other GUI screens corresponding to the individual treatment-information fields, can include one or more of "Battery" GUI tab 410; "Stimulation Lead Impedance" GUI tab 415; "Therapy Duration" GUI tab 420; "24-Hour Pitch" GUI tab 425; "24-Hour Activity" GUI tab 430; "Overnight Efficacy" GUI tab 435; "Capture Analysis" GUI tab 440; "Activity Trend" GUI tab 445; "Waveform Browser" GUI tab 450; "Print" GUI tab 455; and/or a diagnostic-reporting-and-monitoring-information field, for example, a "Diagnostic Reporting & Algorithm Monitoring" GUI tab 460. These GUI treatment-information fields are provided as examples only, and it must be understood that various disclosed embodiments need not include all of these example treatment-information fields and/or can include other (for example, additional, different, or fewer) treatment-information fields.

In one example, selection of a diagnostic-and-monitoring-information field, for example the Diagnostic Reporting & Algorithm Monitoring GUI tab 460, may cause display of a diagnostic-reporting-and-monitoring screen. A diagnostic-reporting-and-monitoring screen may provide patient diagnostics over a selectable period of time including at least a portion of a therapy time. For example, responsive to detecting a user-input signal associated with (for example, indicating a user selection of) the Diagnostic Reporting & Algorithm Monitoring GUI tab 460, the program modules or applications 132 of computing device 100 may configure the processing unit 102 to provide, on display device 116, a diagnostic-reporting-and-monitoring screen.

Figure 5:
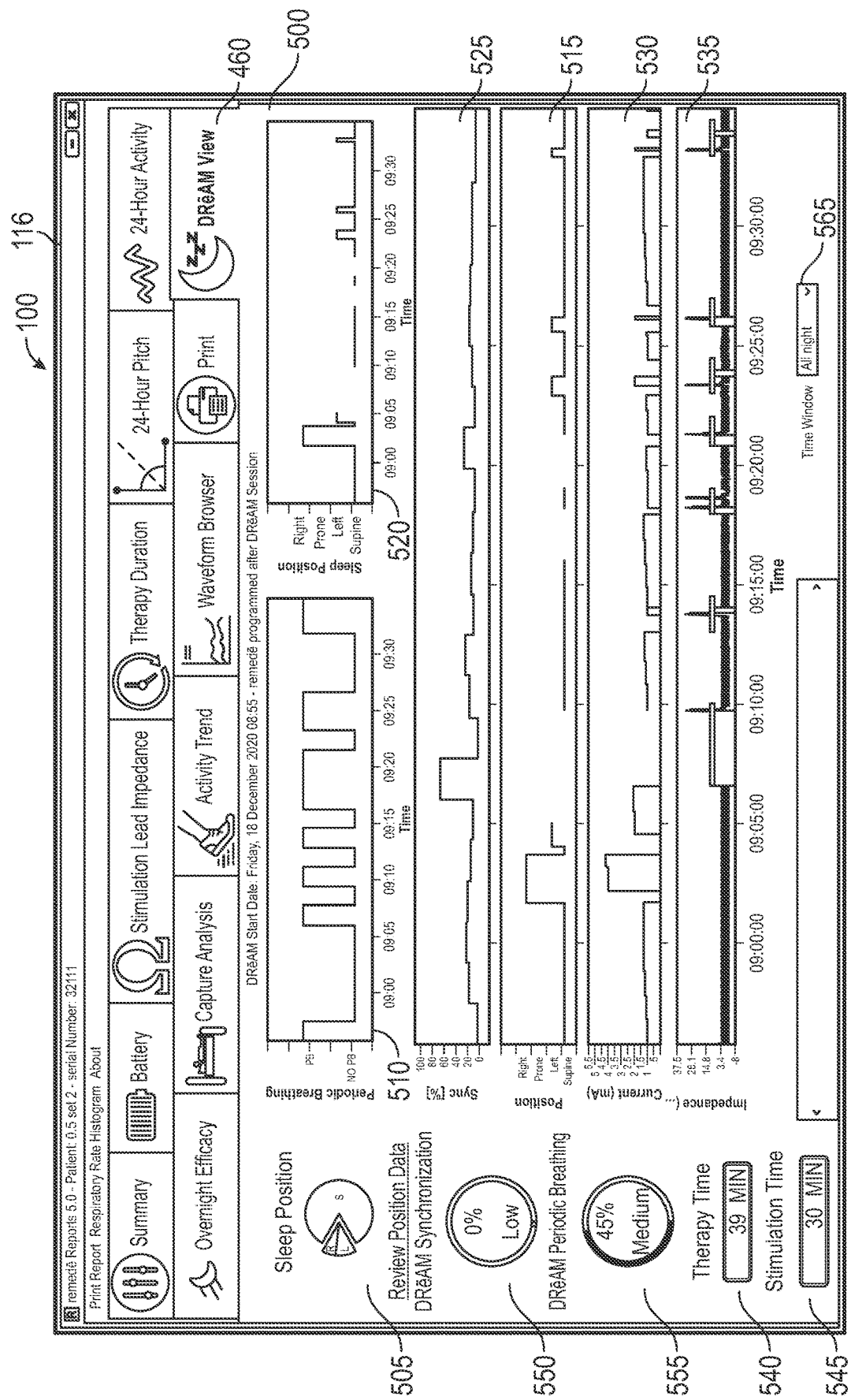
FIG. 5 is an illustration of an exemplary Diagnostic Reporting & Algorithm Monitoring GUI screen, which the computing device shown in FIGS. 1 and 2 is configured to display, to provide a snapshot of trends for various parameters related to the therapy being provided to the patient.

Referring now to FIG. 5, one example of a diagnostic-reporting-and-monitoring screen includes a Diagnostic Reporting & Algorithm Monitoring GUI screen 500, which may be displayed responsive to detecting a user-input signal associated with a diagnostic-and-monitoring-information field of the plurality of treatment-information fields, for example the tab 460, as discussed above. The GUI screen 500, which may be generated using program modules or applications 132 to configure processing unit 102 to control display 116, provides visual renderings of therapy information indicative of trends or time-domain signals for various parameters related to the therapy being provided to the patient. The therapy information may be provided to a user, such as a patient or clinician. The therapy information may advantageously provide a summary view (or "snapshot") of various parameters related to the therapy to a user. The user may thus quickly understand and assess the efficacy of the therapy using the therapy information. In some examples, the user may make modifications to the therapy based at least in part on the therapy information.

In various examples, the therapy information may correspond to a user-selected period of time, such as an entire night during which therapy is applied, an hour of time during which therapy is applied, and so forth. The selected period of time may include any period of time in some examples, and may include some, all, or none of the time during which therapy is applied. In some examples, the selected period of time may include one or more periods of time during which therapy is applied and one or more periods of time during which therapy is not applied, and the GUI screen 500 may automatically display information corresponding only to those one or more periods of time during which therapy is applied. A user may select a period of time over which to view therapy-information-related illustrations using a time-window-selection input 565 in various examples.

The therapy information represented in GUI screen 500 can include, for example, patient-diagnostic data such as described in U.S. Pat. No. 8,233,987, titled RESPIRATORY RECTIFICATION. For example, the GUI screen 500 may include a first sleep-position illustration 505 and a second sleep-position illustration 520. The first sleep-position illustration 505 illustrates a pie chart indicating a proportion of time that a patient spent in each of one or more sleeping positions throughout a selected period of time. For example, the one or more sleeping positions may include a right-side position, a left-side position, a supine position, and a prone position. Information indicative of the one or more sleeping positions may be advantageous at least because a user, such as a clinician, may evaluate an effectiveness of therapy for each sleeping position. In some examples, a clinician may evaluate the effectiveness of therapy at least in part by considering respiration synchronization. For example, if the user determines that respiration synchronization is high while the patient is in a supine position, but lower in the prone position, the user may focus treatment efforts on increasing respiration synchronization in the prone position. In the example illustrated by the first sleep-position illustration 505, the patient may have spent a majority of the selected period of time in the supine position, with lesser (and substantially similar) amounts of time in the left-side and right-side positions.

The second sleep-position illustration 520 illustrates a plot indicating a sleep position of the patient throughout the selected period of time. In various examples, whereas the first sleep-position illustration 505 illustrates a total amount of time spent in each of one or more sleeping positions throughout the selected period of time, the second sleep-position illustration 520 illustrates a sleep position of the patient over time. The second sleep-position illustration 520 includes a trace indicating, at any given point over the selected period of time, whether the patient is determined to be in the right-side position, the left-side position, the prone position, or the supine position. In various examples, the trace may be omitted for times at which information is unavailable.

A first periodic-breathing illustration 510 illustrates a plot indicating a presence or absence of periodic breathing throughout the selected period of time. Periodic breathing may be determined to be present where a patient experiences periods of hyperpnea and/or hypopnea rather than experiencing consistent breathing patterns. As discussed in greater detail below, periodic breathing may be a symptom of any of several conditions. It may be advantageous to minimize or eliminate periods of periodic breathing. The first periodic-breathing illustration 520 may therefore indicate an effectiveness of therapy, as evidenced by the absence of periodic breathing. The first periodic-breathing illustration 520 includes a trace indicating, at any given point over the selected period of time, whether the patient is experiencing periodic breathing. For example, the trace may be in a first position indicating the presence of periodic breathing, or may be in a second position indicating an absence of periodic breathing.

As noted above, periodic breathing may be a symptom of any of several conditions. During sleep, respiratory control may be unconscious and governed by metabolic demand (including, for example, the need to remove $CO_2$ from blood). In all humans, the central neural drive to the respiratory pump and airway muscles during sleep may be reduced compared to an awake state. In the presence of a pathology, airway resistance to airflow can be increased during sleep resulting in, for example, snoring. In some cases, the airway can close completely resulting in obstructive sleep apnea (OSA). In some cases, deregulation of the central control can result in periodic breathing and severe disease that can damage multiple organs.

Central Sleep Apnea (CSA) is a form of periodic breathing characterized by an oscillating central respiratory drive. CSA may be characterized by a typical waxing and waning respiratory pattern made up of alternating apneas or hypopneas and hyperpneas (periods of hyperventilation), historically called Cheyne-Stokes Respiration (CSR). OSA is characterized by upper airway instability. A collapsed airway prevents or reduces inspiration in the face of continuing or increasing respiratory effort. A common pattern of OSA in the general population is characterized by periodic arousals that may result in abrupt opening of the airway. In some patient populations, such as those with congestive heart failure (CHF) for example, it is difficult if not impossible to separate the underlying mechanisms of OSA and CSA. A purely central CSR pattern is somewhat rare. Common presentation of periodic breathing in CHF patients may consist of alternating respiratory events that can include hyperpneas, hypopneas, and central, obstructive, and mixed apneas. A significant overlap exists, and most patients experience varying degrees of both central and obstructive events.

It may be advantageous to visually render certain data along a common time scale and visually align the visually rendered data along the common time scale. For example, it may be advantageous to display several illustrations with a substantially similar or identical time scale such that the parameters indicated by the illustrations can be interpreted with respect to one another. In one example, a diagnostic-reporting-and-monitoring screen, for example the GUI screen 500, may visually render sleep-position data indicative of a sleeping position of a selected patient along a time scale. The time scale may be, or may be displayed along, for example, an axis (for example, an x-axis) of the visual rendering, and the time scale may include at least a portion of a therapy time. The sleep-position data may indicate, for example, that a patient is sleeping in a right-side position, a left-side position, a prone position, a supine position, and so forth. The diagnostic-reporting-and-monitoring screen may also visually render patient-breathing data indicative of breathing patterns of the selected patient along the same time scale (for example, by having the same x-axis corresponding to time). The diagnostic-reporting-and-monitoring screen may visually align the time scale of the sleep-position data and the time scale of the patient-breathing data, such as by visually aligning an x-axis of the sleep-position data with the x-axis of the patient-breathing data. The patient-breathing data may indicate, for example, respiration-synchronization data, periodic-breathing data, stimulation-energy data (for example, indicative of a stimulation current or energy provided to a user to affect patient breathing), and so forth. In some examples, one or more illustrations of different patient-breathing data may be displayed and visually aligned with one or more illustrations of sleeping-position data. For example, sleeping-position data may be visually rendered and visually aligned with a first visual rendering of patient-breathing data (for example, indicative of periodic-breathing data) and with a second visual rendering of patient-breathing data (for example, indicative of respiration-synchronization data). At least because the sleep-position data may be visually aligned with the patient-breathing data along the time scale, a user may easily compare sleep-position and patient-breathing data at any given time along the time scale.

The GUI screen 500 includes a first synchronization illustration 525, a third sleep-position illustration 515, a stimulation-current illustration 530, and a breathing-impedance illustration 535, each of which may display information along a time scale represented by a respective x-axis. The GUI screen 500 may display the illustrations 515, 525, 530, 535 such that the illustrations 515, 525, 530, 535 are visually aligned along the time scale, that is, along the x-axis. Accordingly, the parameters indicated by the illustrations may be visually evaluated relative to one another at a given time at least in part because of the visual alignment along the x-axis. Although certain parameters are indicated by the illustrations for purposes of example, additional, fewer, or different parameters and/or illustrations may be displayed and aligned in other examples.

The first synchronization illustration 525 illustrates a plot indicating respiration synchronization for the patient over time. In one example, the first synchronization illustration 525 may provide an example of visually rendered patient-breathing data indicative of breathing patterns of a selected patient, as discussed above. For example, patient-breathing data may include respiration-synchronization data. A trace indicates a respiration synchronization of the patient at a given time along a time scale represented by the x-axis, which may be depicted as a percentage of respiration synchronization. Respiration-synchronization indices may provide a measure of therapy effectiveness. Respiration synchronization may indicate a synchronization between a patient's breathing and an application of a stimulation current to the patient. In various examples, if the patient's breathing is aligned with the application of the stimulation current (that is, if synchronization is high), the patient may be responding to therapy. Conversely, if the patient's breathing is not aligned with the application of the stimulation current (that is, synchronization is low), the patient may not be responding to therapy. In some examples, a respiration-synchronization index may be calculated by dividing spectral power around a given respiratory rate band (that is, a frequency band in which stimulation pulse trains are applied to a patient) over a given period of time (for example, a rolling window of time) by spectral power in the respiratory frequency band or a subset of the respiration frequency band (that is, a natural respiratory frequency of a patient, such as 10-30 breaths per minute, or 0.16-0.5 Hz) over the given period of time.

Synchronization indices can be calculated using different techniques and used in the treatment of disordered breathing. U.S. Pat. No. 8,233,987, titled RESPIRATORY RECTIFICATION, discloses some of these techniques. For example, the intrinsic breathing rate or frequency of the patient can be determined, and one hemidiaphragm of the patient can be stimulated at a frequency different from the intrinsic breathing frequency. A frequency analysis of the respiration signal during stimulation can be conducted, and a synchronization index can be determined by dividing the power distribution in a frequency range proximate the stimulation frequency to the power of the range of frequencies consistent with respiration to determine the respiration synchronization index. Stimulation parameters may be modified based on the calculated respiration synchronization index. In some embodiments, the signal representative of respiration may be transthoracic impedance. In some embodiments, the stimulation frequency is lower than the intrinsic breathing frequency. In some embodiments, the stimulation power is increased if the respiration synchronization index is below a certain threshold. In some embodiments, the stimulation power is decreased if the respiration synchronization index is above a certain threshold. In some embodiments, the stimulation power is kept unchanged if the respiration synchronization index remains within a certain range. Other methods and techniques of calculating a respiration synchronization index can also be utilized.

The third sleep-position illustration 515 illustrates a plot indicating a sleep position of the patient throughout the selected period of time. In one example, the third sleep-position illustration 515 may provide an example of visually rendered sleep-position data indicative of a sleeping position of a selected patient, as discussed above. The third sleep-position illustration 515 includes a trace indicating, at any given point along a time scale represented by the x-axis, whether the patient is determined to be in the right-side position, the left-side position, the prone position, or the supine position. In various examples, the trace may be omitted for times at which information is unavailable. In one example, the third sleep-position illustration 515 and the first synchronization illustration 525 may each display information along a common time scale, and may be visually aligned along the common time scale. As discussed above, sleep-position data may be visually rendered along a time scale, for example the third sleep-position illustration 515, and patient-breathing data may be visually rendered along the same time scale and visually aligned with the time scale of the sleep-position data, for example the first synchronization illustration 525.

The third sleep-position illustration 515 may display substantially similar or identical information as the second sleep-position illustration 520 in some examples. However, at least because the third sleep-position illustration 515 is visually aligned with the first synchronization illustration 510 along the x-axes thereof, a user may glean additional information from the third sleep-position illustration 515. For example, the user may observe that certain sleeping positions are associated with higher or lower synchronization, and evaluate the effectiveness of therapy for each sleeping position based on these observations. In one example, if the user observes that a right-side sleeping position is associated with high synchronization, the user may determine that the therapy is effective while the user in the right-side sleeping position. Conversely, if the user observes that a prone sleeping position is associated with lower synchronization, the user may determine that therapy is less effective while the user is in the prone sleeping position. Accordingly, the ability to correlate different therapy information at given periods of time enables a user to glean additional information from the therapy information. That is, certain synergies may be attained whereby additional information is available from a combination of information than is available from a sum of the constituent information.

The stimulation-current illustration 530 illustrates a plot indicating a stimulation current over time. The stimulation current may be a current applied through an implanted device, such as via the stimulation lead 14. A trace indicates a magnitude of stimulation current provided to the one or more electrodes. The stimulation-current illustration 530 may advantageously enable a user to determine whether a stimulation current is too high or too low, for example, at various points in time and for various sleeping positions. In one example, the stimulation-current illustration 530 may provide an example of the patient-breathing data discussed above, and may be visually aligned with the illustrations 515 and/or 525 along a common time scale as discussed above.

The breathing-impedance illustration 535 illustrates a plot indicating a transthoracic impedance of the patient over time. The transthoracic impedance may be indicative of respiration of the patient. For example, the transthoracic impedance may be indicative of lung volume of the patient. In one example, the transthoracic impedance is measured between the control device 12 and the transthoracic lead 16 and/or the stimulation lead 14. A trace indicates a magnitude of transthoracic impedance of the patient over time. In one example, the breathing-impedance illustration 535 may provide an example of the patient-breathing data discussed above, and may be visually aligned with the illustrations 515, 525, and/or 535 along a common time scale as discussed above.

As discussed above, the illustrations 515, 525, 530, 535 may include additional, fewer, or different illustrations and/or illustrations depicting additional, less, or different therapy information, including additional, less, or different sleep-position data and/or patient-breathing data. For example, the GUI tab 460 may alternately or additionally display information indicative of one or more treatment-device angles (for example, a pitch angle, roll angle, and/or yaw angle of the treatment system 10), one or more apnea-detection flags (for example, overlaid on time-domain information), one or more periodic-breathing-detection flags (for example, overlaid on time-domain information), heart-rate information, and so forth. Furthermore, a time scale along a common x-axis shared by the vertically aligned illustrations may be variable and/or user selectable. Accordingly, it is to be appreciated that the examples of FIG. 5 are not to be construed as limiting on a type and/or amount of information that may be displayed.

The GUI screen 500 further includes a second synchronization illustration 550 illustrating an amount of respiration synchronization over a period of time. For example, the second synchronization illustration 550 may depict a percentage of time that the patient's respiration is synchronized. The percentage may be a percentage of time that the patient's respiration is synchronized above a threshold value, such as 75%, 90%, 99%, and so forth, in one example. In another example, the percentage may be an average of the percentage of respiration synchronization (for example, as illustrated by the first synchronization illustration 525) over a given period of time. In some examples, the second synchronization illustration 550 may additionally or alternatively display a classification or evaluation of an amount of respiration synchronization. For example, the classifications may include "Low," "Medium," "High," and so forth, each corresponding to a range of percentage values. In one example, as illustrated by FIG. 5, a respiration-synchronization percentage of 0% may be classified as "Low." In other examples, other classifications and/or methods of classifying may be implemented.

The GUI screen 500 further includes a second periodic-breathing illustration 555 illustrating an amount of periodic breathing over a period of time. For example, the second periodic-breathing illustration 555 may depict a percentage of time over the period of time that the patient is experiencing periodic breathing. In some examples, the second periodic-breathing illustration 555 may additionally or alternatively display a classification or evaluation of an amount of periodic breathing. For example, the classifications may include "Low," "Medium," "High," and so forth, each corresponding to a range of percentage values. In one example, as illustrated by FIG. 5, a periodic-breathing percentage of 45% may be classified as "Medium." In other examples, other classifications and/or methods of classifying may be implemented.

The GUI screen 500 further includes a therapy-time illustration 540 illustrating an amount of time that therapy is conducted. A time that therapy is conducted may include periods during which stimulation is applied and periods during which stimulation is not applied. Accordingly, in some examples, the total therapy time may be longer than a total stimulation time. In one example, the therapy time indicated by the therapy-time illustration 540 is a subset of a total therapy time (for example, one subset of time throughout an entire night during which therapy is applied), which may be selected by a user, such as a clinician reviewing a particular portion of therapy. In one example illustrated by FIG. 5, a therapy time may be 39 minutes.

The GUI screen 500 further includes a stimulation-time illustration 545 illustrating a total amount of time that stimulation is applied. Stimulation time may include a total time during which a stimulation current is applied via a device, such as via the stimulation lead 14. In some examples, stimulation time may include a total time during which a stimulation current above a certain threshold current is applied, such that low stimulation currents (for example, currents below the threshold current) do not contribute towards the total time during which a qualifying stimulation current is applied. In one example, the stimulation time indicated by the stimulation-time illustration 545 is a subset of a total stimulation time (for example, one subset of time throughout an entire night during which stimulation is applied), which may be selected by a user, such as a clinician reviewing a particular portion of therapy. In one example illustrated by FIG. 5, a stimulation time may be 30 minutes.

Figure 6:
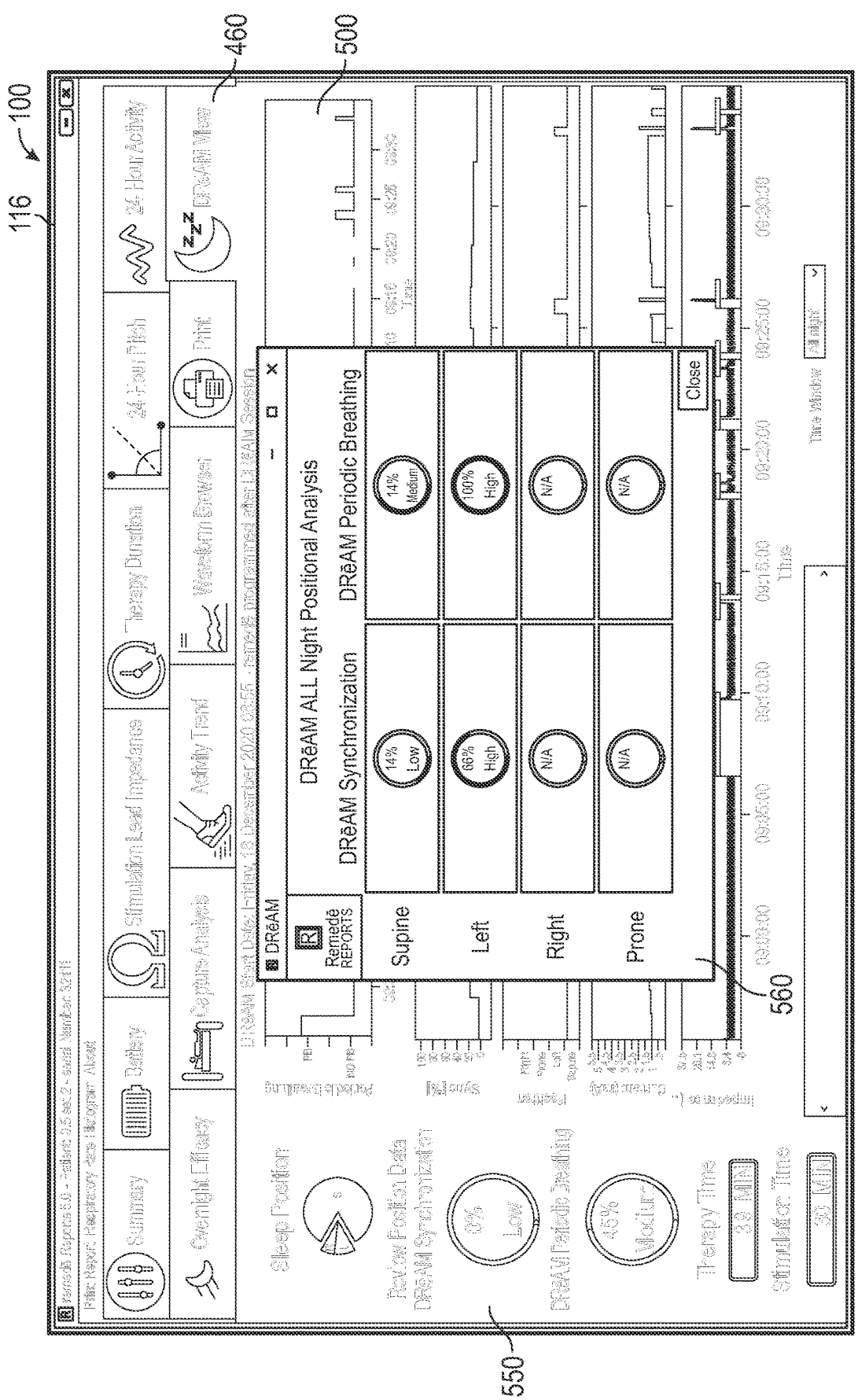
FIG. 6 is an illustration of the exemplary Diagnostic Reporting & Algorithm Monitoring GUI screen shown in FIG. 5, with a pop-up showing positional analysis data for synchronized respiratory activity and periodic breathing for the patient.

In exemplary embodiments, the GUI screen 500 may display additional or different illustrations responsive to receiving a user input interacting with one or more illustrations or other user-interface elements. The GUI screen 500 may display, via a pop-up or other auxiliary display, sleep-position data based on patient-breathing data, and/or may display patient-breathing data based on sleep-position data. For example, in an example in which the sleep-position data indicates various sleeping positions for a patient, patient-breathing data may be separated and displayed based on each sleeping position of the various sleeping positions. For example, FIG. 6 illustrates a pop-up, for example a pop-up 560, which may be displayed responsive to receiving a user input (for example, a "double-click" input, a tapping input, and so forth) selecting at least one of the illustrations 550, 555. The pop-up 560 may overlay at least a portion of the GUI screen 500.

A pop-up displayed by the GUI screen 500, for example the pop-up 560, may depict patient-breathing data based on (for example, filtered according to) sleep-position data. The patient-breathing data may include, for example, information indicative of respiration synchronization over a given period of time and/or indicative of periodic breathing over the given period of time. The sleep-position data may include, for example, one or more sleeping positions, such as a right-side sleeping position, a left-side sleeping position, a supine sleeping position, and/or a prone sleeping position. In some examples, the type of information displayed on a pop-up may be substantially similar or identical to the information illustrated by the illustrations 550, 555, except that the pop-up, for example the pop-up 560, may depict patient-breathing information corresponding to each respective sleeping position. A user, such as a clinician, may be able to more easily evaluate an effectiveness of therapy for each sleeping position by reviewing an amount of respiration synchronization and periodic breathing for each sleeping position. For example, the user may observe that the patient experiences 100% periodic breathing while in the left-side sleeping position and therefore adjust therapy corresponding to the left-side sleeping position.

In some examples, a pop-up (for example, the pop-up 560) may depict information that is similar to the information illustrated by the illustrations 550, 555, but over a different (for example, longer or shorter) time scale. For example, in one non-limiting example, the illustrations 550, 555 may display information corresponding to a first time period (for example, a time period corresponding to a selection made at the time-window-selection input 565) and the pop-up may display information corresponding to a second time period (for example, an entire night over which therapy may be applied), which may be different than the first time period. In other examples, information may be displayed for other periods of time, which may be user-configurable in some examples.

Figure 7:
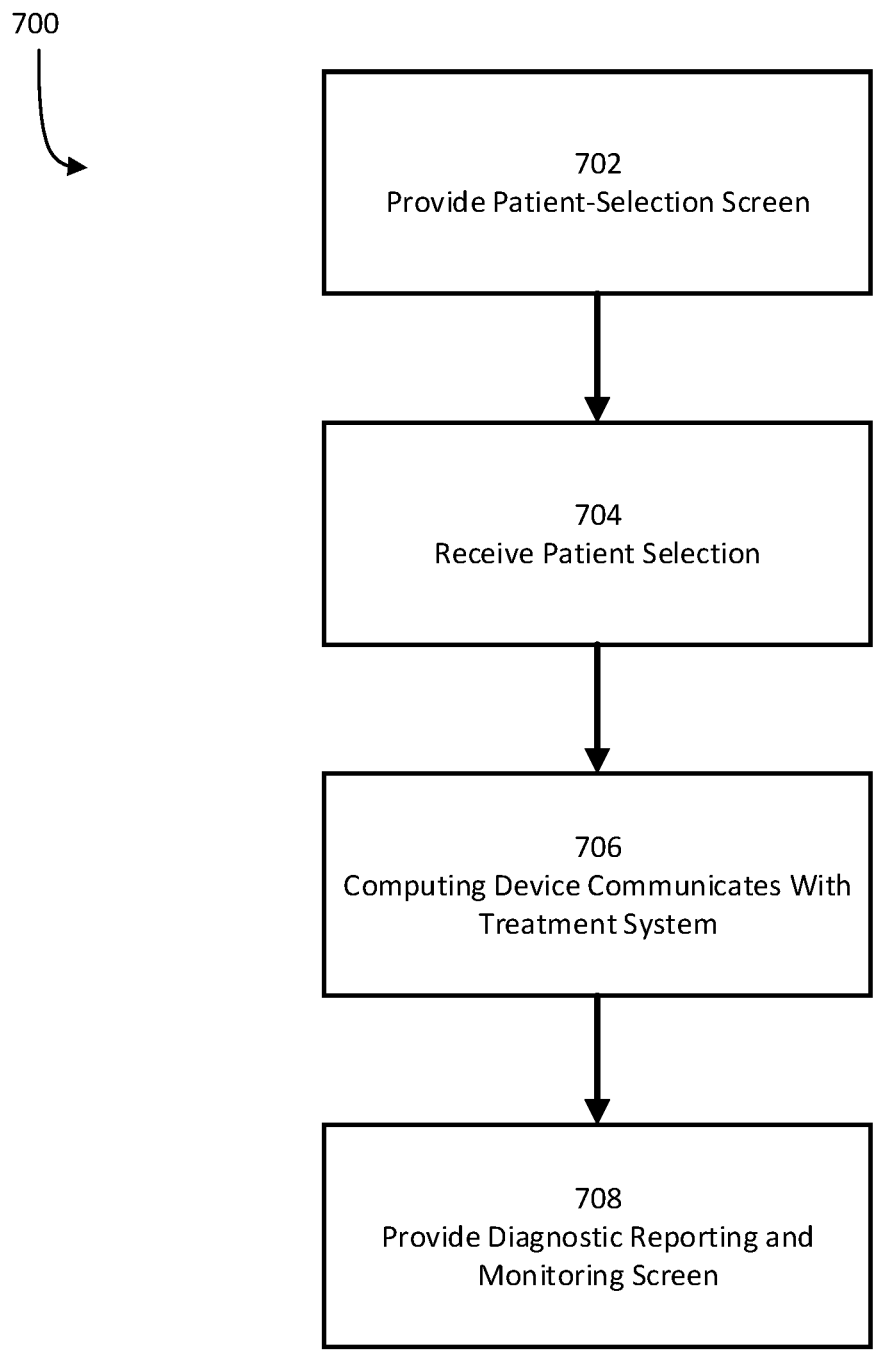
FIG. 7 illustrates a process of providing therapy information according to an example.

FIG. 7 illustrates a process 700 of providing therapy information according to an example. The process 700 may be executed by a computing device, such as the computing device 100, in connection with a treatment system, such as the treatment system 10.

Figure 3:
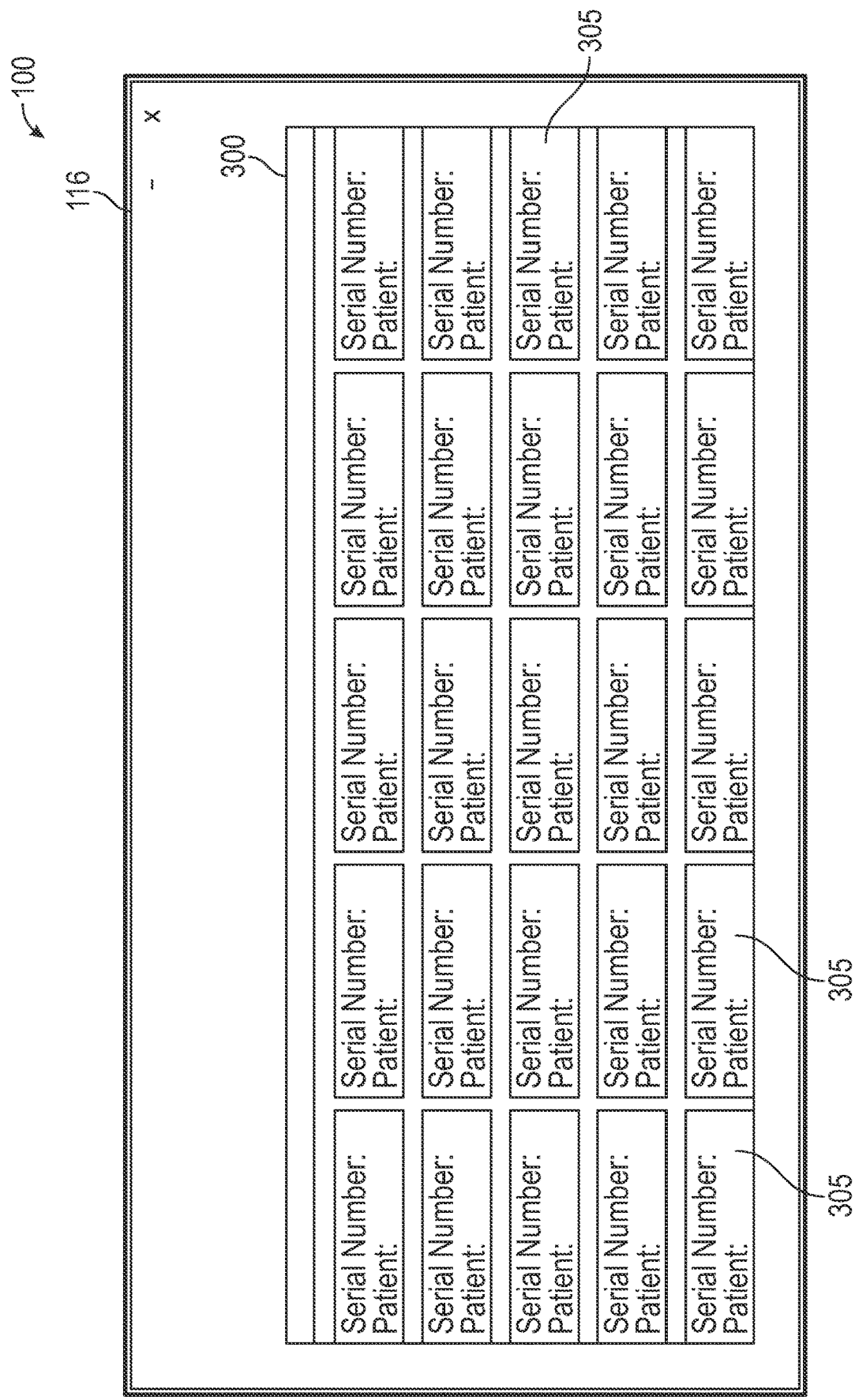
FIG. 3 is an illustration of an exemplary patient selection GUI screen, which the computing device shown in FIGS. 1 and 2 is configured to display, to allow a user to select a particular patient.

At act 702, a patient-selection screen is provided to a user. For example, the patient-selection screen may be the patient-selection GUI screen 300 illustrated above with respect to FIG. 3. The patient-selection screen may provide information indicative of one or more patients and other information associated with the patients, such as the patients' names, identification numbers, and so forth.

At act 704, a selection of a patient is received. For example, as discussed above, the received patient selection may include a "clicking" user input on a selected patient, or other known user-input mechanisms.

At act 706, the computing device communicates with the treatment system to obtain patient data from the treatment system. For example, the computing device 100 may communicate with the treatment system 10 via the communication connection 30 to request patient data from the treatment system 10. As discussed above, patient data may include, for example, information indicative of therapy administered to a patient, such as sleeping-position data, stimulation current, transthoracic impedance, and so forth.

At act 708, the computing device provides a diagnostic reporting and monitoring screen on a display device based on the patient data. For example, the computing device 100 may provide, by an application running on the computing device 100, the GUI screen 500 on the display device 116. As discussed above, the GUI screen 500 may display information including graphical illustrations indicative of sleep-position data for a selected patient, either alone or in combination with one or more additional graphical illustrations of other data for the selected patient. The displayed graphical illustrations may include, for example, any of the illustrations depicted and discussed above with respect to FIGS. 5 and 6. For example, the one or more additional graphical illustrating may display respiration-synchronization information, stimulation-current information, impedance information, and so forth.

Although the present disclosure has been described with reference to preferred embodiments, workers skilled in the art will recognize that changes may be made in form and detail without departing from the spirit and scope of the disclosure.

What is claimed is:

1. A method to aid a user monitoring of a disordered-breathing treatment, the method comprising:
    displaying, by at least one processor on a user-computing-device screen of a user computing device, a patient-selection screen including a plurality of patient-selection fields, each patient-selection field corresponding to a respective patient of a plurality of selectable patients;
    receiving, via the patient-selection screen, an input from a user indicative of a selection of the respective patient selected by the user and corresponding to the patient-selection field of the plurality of patient-selection fields;

communicating between the user computing device and a treatment system implanted in the selected respective patient, responsive to receipt of the input indicative of the selection of the respective patient, to receive and process patient data from the treatment system to the user computing device;

displaying, by the user computing device, a plurality of treatment-information fields, wherein each treatment-information field of the plurality of treatment-information fields corresponds to treatment information of the selected respective patient and is selectable via a respective treatment-information-field portion of the patient-selection screen; and displaying, by the user computing device responsive to detecting a user-input signal associated with a diagnostic-reporting-and-monitoring-information field of the plurality of treatment-information fields, a diagnostic-reporting-and-monitoring screen including
sleep-position data indicative of a sleeping position of the selected respective patient, the sleep-position data being visually rendered along a time scale that includes at least a therapy time, and
patient-breathing data indicative of breathing patterns of the selected respective patient, the patient-breathing data being visually rendered along the time scale that includes the therapy time and being visually rendered relative to the sleep-position data such that the time scale of the patient-breathing data is visually aligned with the time scale of the sleep-position data.

2. The method of claim 1, wherein the patient-breathing data includes respiration-synchronization data for the selected respective patient.

3. The method of claim 2, wherein visually rendering the patient-breathing data includes displaying the respiration-synchronization data plotted as a function of time.

4. The method of claim 2, wherein visually rendering the patient-breathing data includes displaying synchronized respiratory activity of the selected respective patient as a percentage.

5. The method of claim 4, wherein the patient-breathing data includes periodic-breathing data for the selected respective patient.

6. The method of claim 5, wherein visually rendering the patient-breathing data includes displaying the periodic-breathing data for the selected respective patient as a percentage.

7. The method of claim 5, further comprising:
displaying, by the user computing device and responsive to detecting a user-input signal associated with at least one of the sleep-position data or the patient-breathing data, a pop-up screen overlaying portions of the diagnostic-reporting-and-monitoring screen, the pop-up screen visually rendering synchronized-respiratory-activity data and periodic-breathing data in relation to sleep position of the selected respective patient.

8. The method of claim 1, wherein the patient-breathing data includes periodic-breathing data for the selected respective patient.

9. The method of claim 1, wherein the patient-breathing data includes stimulation-energy data applied to the selected respective patient by the treatment system.

10. The method of claim 9, wherein the patient-breathing data includes stimulation-current data indicative of a stimulation current applied to the selected respective patient by the treatment system.

11. A monitoring system for monitoring disordered breathing treatment of a patient with a disordered-breathing-treatment system implanted in the patient, the monitoring system comprising:
communication components configured to establish a communication link between the monitoring system and the disordered-breathing-treatment system implanted in the patient;
a display device configured to display a graphical user interface (GUI) for use by a user of the monitoring system; and
at least one processor configured to:
control the display device to display a patient-selection screen including a plurality of patient-selection fields, each patient-selection field corresponding to a respective patient of a plurality of selectable patients;
receive, via the patient-selection screen, an input from the user indicative of a selection of the respective patient selected by the user and corresponding to the patient-selection field of the plurality of patient-selection fields;
communicate between the at least one processor and a treatment system implanted in the selected respective patient, responsive to receipt of the input indicative of the selection of the respective patient, to receive and process patient data from the treatment system to the at least one processor;
control the display device to display a plurality of treatment-information fields, wherein each treatment-information field of the plurality of treatment-information fields corresponds to treatment information of the selected respective patient and is selectable via a respective treatment-information-field portion of the patient-selection screen; and
control the display device to display, responsive to detecting a user-input signal associated with a diagnostic-reporting-and-monitoring-information field of the plurality of treatment-information fields, a diagnostic-reporting-and-monitoring screen including
sleep-position data indicative of a sleeping position of the selected respective patient, the sleep-position data being visually rendered along a time scale that includes at least a therapy time, and
patient-breathing data indicative of breathing patterns of the selected respective patient, the patient-breathing data being visually rendered along the time scale that includes the at least the therapy time and being visually rendered relative to the sleep-position data such that the time scale of the patient-breathing data is visually aligned with the time scale of the sleep-position data.

12. The monitoring system of claim 11, wherein the patient-breathing data includes respiration-synchronization data for the selected respective patient.

13. The monitoring system of claim 12, wherein visually rendering the patient-breathing data includes displaying the respiration-synchronization data plotted as a function of time.

14. The monitoring system of claim 11, wherein the patient-breathing data includes periodic-breathing data for the selected respective patient.

15. The monitoring system of claim 11, wherein the patient-breathing data includes stimulation-energy data indicative of stimulation energy applied to the selected respective patient by the treatment system.

16. A non-transitory computer-readable medium storing thereon sequences of computer-executable instructions for aiding in user monitoring of a disordered-breathing treatment, the sequences of computer-executable instructions including instructions that instruct at least one processor to:
   display, by at least one processor on a user-computing-device screen of a user computing device, a patient-selection screen including a plurality of patient-selection fields, each patient-selection field corresponding to a respective patient of a plurality of selectable patients;
   receive, via the patient-selection screen, an input from a user indicative of a selection of the respective patient selected by the user and corresponding to the patient-selection field of the plurality of patient-selection fields;
   communicate between the user computing device and a treatment system implanted in the selected respective patient, responsive to receipt of the input indicative of the selection of the respective patient, to receive and process patient data from the treatment system to the user computing device;
   display, by the user computing device, a plurality of treatment-information fields, wherein each treatment-information field of the plurality of treatment-information fields corresponds to treatment information of the selected respective patient and is selectable via a respective treatment-information-field portion of the patient-selection screen; and
   display, by the user computing device responsive to detecting a user-input signal associated with a diagnostic-reporting-and-monitoring-information field of the plurality of treatment-information fields, a diagnostic-reporting-and-monitoring screen including
      sleep-position data indicative of a sleeping position of the selected respective patient, the sleep-position data being visually rendered along a time scale that includes at least a therapy time, and
      patient-breathing data indicative of breathing patterns of the selected respective patient, the patient-breathing data being visually rendered along the time scale that includes the at least the therapy time and being visually rendered relative to the sleep-position data such that the time scale of the patient-breathing data is visually aligned with the time scale of the sleep-position data.

17. The non-transitory computer-readable medium of claim 16, wherein the patient-breathing data includes respiration-synchronization data for the selected respective patient.

18. The non-transitory computer-readable medium of claim 17, wherein visually rendering the patient-breathing data includes displaying the respiration-synchronization data plotted as a function of time.

19. The non-transitory computer-readable medium of claim 17, wherein visually rendering the patient-breathing data includes displaying respiratory activity as a percentage.

20. The non-transitory computer-readable medium of claim 19, wherein the patient-breathing data includes periodic-breathing data for the selected respective patient.

* * * * *